US006777573B1

(12) United States Patent
Khrimian

(10) Patent No.: US 6,777,573 B1
(45) Date of Patent: Aug. 17, 2004

(54) METHOD FOR THE SYNTHESIS OF CERALURE B1

(75) Inventor: Ashot Khrimian, Rockville, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 109 days.

(21) Appl. No.: 10/254,502

(22) Filed: Sep. 26, 2002

(51) Int. Cl.$^7$ .................. C07C 229/00; C07C 61/08
(52) U.S. Cl. ................................. 560/125; 562/507
(58) Field of Search ................. 562/507; 560/125

(56) References Cited

U.S. PATENT DOCUMENTS

| | | | |
|---|---|---|---|
| 3,016,329 A | 1/1962 | Beroza et al. | |
| 4,764,366 A | 8/1988 | McGovern et al. | |
| 6,375,943 B1 | 4/2002 | Raw et al. | |

OTHER PUBLICATIONS

B. A. Leonhardt et al., "Comparison of Ceralure and Trimedlure Attractants for the Male Mediterranean Fruit Fly", *J. Entomol. Sci.*, vol. 31, (2), pp. 183–190, 1996.
J. D. Warthen, Jr. et al., "*Trans*–Ceralure Isomers: Differences in Attraction for Mediterranean Fruit Fly, *Ceratitis capitata* (Wied.) (Diptera: Tephritidae)", *Journal of Chemical Ecology*, vol. 20, (3), pp. 569–578, 1994.

J. W. Avery et al., "Regioselective Synthesis of Ceralure $B_1$ and A, Ethyl cis–(and trans–) 5–Iodo–5–Iodo–*trans*–2–Methylcyclohexane–1–Carboxylate", *Tetrahedron Letters*, vol. 35, (50), pp. 9337–9338, 1994.

A. S. Raw et al., "Enantioselective Synthesis of Ceralure $B_1$, Ethyl cis–5–Iodo–*trans*–2–methylcyclohexane–1–carboxylate", *Tetrahedron*, vol. 56, pp. 3285–3290, 2000.

*Primary Examiner*—Johann Richter
*Assistant Examiner*—Paul A. Zucker
(74) *Attorney, Agent, or Firm*—John D. Fado; G. Byron Stover

(57) ABSTRACT

A method has been developed for the preparation of ceralure B1, a potent attractant for the Mediterranean fruit fly. The method utilizes trans-siglure acid as starting material to produce iodolactone which is subsequently reduced to lactone. The lactone is converted to a mixture of epimers ceralure A acid and ceralure B1 acid. The ceralure A acid is recyclized to lactone, leaving epimer ceralure B1 acid intact. Following separation from lactone, the ceralure B1 acid is esterified to produce ceralure B1 of about 92–94% purity. The overall yield is about 58–65%, a significant improvement over currently known methods which result in yields of about 30–33%.

4 Claims, 1 Drawing Sheet

METHOD FOR THE SYNTHESIS OF CERALURE B1

BACKGROUND OF THE INVENTION

1. Field of the Invention

The Mediterranean fruit fly, *Ceratitis capitata* (Wiedemann) is a worldwide agricultural pest affecting over 253 varieties of fruits and vegetables (Liquido et al. 1991. *Misc. Publ. Entomol. Soc. Am.* vol. 77, p. 1). The invention relates to a method for the synthesis of ceralure B1, a strong attractant for *C. capitata* which is used in traps to monitor and detect the insects.

2. Description of the Relevant Art

The Mediterranean fruit fly, commonly known as medfly, is found in tropical areas such as central America and Hawaii. Periodic accidental introductions of the pests into the continental United States have been controlled by an extensive trapping system which relies on an effective attractant for detecting and monitoring the insects. Due to these and other efforts such as Sterile Insect Technique (SIT), to date the U.S. remains free of established populations. The establishment of the pest in the U.S. would have serious agricultural ramifications, however, such as an increase in the use of pesticides and associated economic and environmental impacts and a decrease in fruit and vegetable exports, a multi-billion dollar industry (Jackson et al. Winter, 1985. *Bulletin of the ESA.* pp. 29–37).

Conventional trapping systems have utilized traps baited primarily with trimedlure, a synthetic male medfly attractant (Beroza et al., U.S. Pat. No. 3,016,329, 1962), and have generally been effective for detecting and monitoring medfly infestations for more than 30 years. Trimedlure is a mixture of 16 regio- and stereoisomers of tert-butyl esters of 4 (and 5)-chloro-2-methylcyclohexane-1-carboxylate, and over one million dispensers containing 2 grams of trimedlure are produced and sold annually for use as bait in detection traps.

More recently, ceralure, an iodo analog of trimedlure, has shown improved attraction capabilities (McGovern and Cunningham, U.S. Pat. No. 4,764,366, 1988). Comparative studies indicated that ceralure was both more attractive and more persistent than trimedlure in the field (Leonhardt et al. 1996. *J. Entomol. Sci.* vol. 31, no. 2, pp. 183–190). In addition, a study of 4 trans isomers showed that the ceralure B1 isomer was superior to the other three isomers investigated (Warthen et al. 1994. *J. Chem. Ecol.* vol. 20, no. 3, pp. 569–578).

Synthetic methods have been described for the production of ceralure B1 (Avery et al. 1994. *Tetrahedron Letters.* vol. 35, no. 50, pp. 9337–9338; Raw and Jang. 2000. *Tetrahedron.* vol. 56, pp. 3285–3290; Raw and Jang, U.S. Pat. No. 6,375,943, 2002), with yields of ~30–33% from the commercially available trans-siglure acid.

SUMMARY OF THE INVENTION

I have discovered a method for the preparation of ceralure B1 which improves the yield up to about 58–65%, approximately double the yield of currently-known synthetic methods. In addition, the method may circumvent chromatographic separations and is amenable to industrial scale-up. In accordance with this discovery, it is an object of the invention to provide a novel method for the preparation of the synthetic medfly attractant ceralure B1.

DETAILED DESCRIPTION OF THE INVENTION

Figure 1:
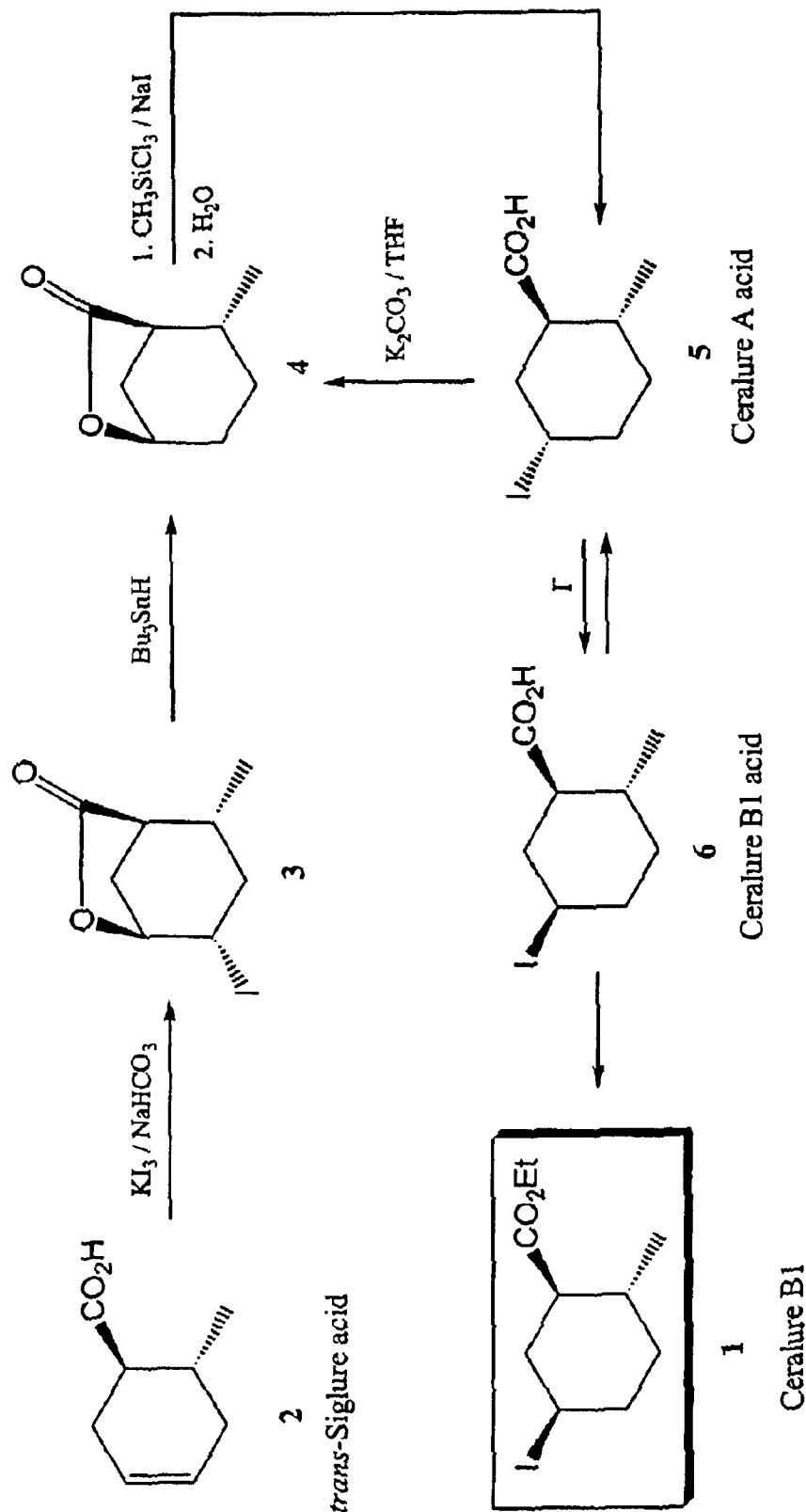
FIG. 1 shows a schematic of the synthesis of ceralure B1.

The compounds involved in the novel process are presented below by both common and chemical names and by numbers as correlated to the compound numbering of the schematic (FIG. 1). Hereinafter the compounds are referred to in the text by common name and number.

| | |
|---|---|
| Ceralure B1 1 | ethyl cis,trans-5-iodo-2-methylcyclohexane-1-carboxylate |
| trans-Siglure acid 2 | trans-6-methyl-3-cyclohexene-1-carboxylic acid |
| Iodolactone 3 | trans,trans-4-iodo-2-methyl-6-oxabicyclo[3.2.1]-octan-7-one |
| Lactone 4 | trans-2-methyl-6-oxabicyclo[3.2.1]octan-7-one |
| Ceralure A acid 5 | trans,trans-5-iodo-2-methylcyclohexane-1-carboxylic acid |
| Ceralure B1 acid 6 | cis,trans-5-iodo-2-methylcyclohexane-1-carboxylic acid |

Ceralure, an iodo analog of trimedlure, both of which are mixtures of 16 regio- and stereoisomers, was found to be a more effective attractant for medfly than trimedlure (McGovern et al., supra). In another study, the ceralure isomers were separated by high performance liquid chromatography (HPLC), the relative attractiveness of the isomers was investigated, and it was demonstrated that ceralure B1 was the most active isomer (Warthen et al., supra).

A regioselective synthesis of ceralure B1 has been described (Avery et al., supra) in which trans-siglure acid 2 was cyclized to iodolactone 3, which was then reduced to lactone 4. The lactone ring was opened with trimethylchlorosilane, and in situ esterification was carried out to provide a mixture of ceralure B1 1 and ceralure A (ethyl trans,trans-5-iodo-2-methylcyclohexane-1-carboxylate) in a ratio of 60:40. The reaction products were reportedly separable by flash chromatography and/or semi-preparative HPLC. Based on the starting material, trans-siglure acid 2, the overall yield of ceralure B1 was about 30%.

More recently, a method of synthesizing ceralure B1 1 was reported by Raw et al. (2000, 2002, supra), also utilizing trans-siglure acid 2 as starting material and following the same initial steps to produce lactone 4 as described by Avery et al., supra. The lactone was further converted by a four-step process to produce ceralure B1 1. The product was isolated by flash chromatography at an approximately 33% yield. The optically active (−)ceralure B1, having about 30% higher attractancy than the racemate, was also synthesized, but the complexity of preparation and low yield precluded its use as a practical lure for medfly.

Thus, both examples in the prior art report relatively low yields and rely on chromatographic methods to isolate ceralure B1 1.

The steps for the novel preparation of ceralure B1 1 are shown in FIG. 1. trans-siglure acid 2 is the starting material, and the first two steps are carried out as described by Avery et al., supra, or Raw et al., supra. Either the racemic or optically active form of the acid may be utilized. For example, (−)-trans-siglure acid may be used as the starting material to produce (−)ceralure B1.

The novel aspect of the invention occurs following conversion of lactone 4 to a mixture of ceralure A acid 5 and ceralure B1 acid 6 where a recycling step occurs: ceralure A acid epimer is cyclized back to lactone 4. By returning unwanted ceralure A acid 5 to lactone via a cyclization step and separating ceralure B1 acid 6 from lactone 4, the overall yield of the product is increased from about 30–33% to about 58–65%. In addition, subsequent conversions of lactone 4 to the mixture of ceralure A acid 5 and ceralure B1 acid 6 may be carried out. At this point, the synthesized ceralure B1 1 is of about 92–94% purity without any chromatographic or other purification steps. If further purification is necessary, ceralure B1 1 (>98%) can be obtained by crystallization of acid 6 followed by esterification.

The synthesis of ceralure B1 1 is thus achieved by carrying out the following steps:

a) converting trans-siglure acid 2 to iodolactone 3, b) reducing iodolactone 3 to lactone 4, c) converting lactone 4 to a mixture of ceralure A acid 5 and ceralure B1 acid 6, d) recycling ceralure A acid 5 to lactone 4 and separating ceralure B1 acid 6, and optionally repeating step c), i.e. converting lactone 4 to a mixture of ceralure A acid 5 and ceralure B1 acid 6, and e) esterifying ceralure B1 acid 6 to produce ceralure B1 1.

The resulting product, ceralure B1 1, is sufficiently pure (about 92–94%) to be utilized without a purification or separation step, however, should higher purity be desired, purity up to >98% may be achieved by chromatography or crystallization.

The individual steps of the synthetic method may be carried out by any effective procedure for each particular step which is known to those of skill in the chemical arts. Specific examples for effectively carrying out the particular steps are provided for convenience.

Steps a) and b), the iodolactonization of trans-siglure acid 2 to iodolactone 3 and the reduction of iodolactone 3 to lactone 4 are published synthetic methods (Avery et al., supra; Raw et al., supra) and are described in Examples 1 and 2.

Opening the lactone 4 ring in step c) may effectively utilize a trimethylchlorosilane/sodium iodide method as described by Avery et al., supra, however, a trichloromethylsilane/sodium iodide mixture has been found to be more efficient (see Examples 3 and 6). The cleavage of lactone 4 appears to be highly stereoselective, occurring by inversion of the configuration at C-3. At the beginning of the reaction, ceralure A acid 5 is formed exclusively after hydrolysis of an intermediate silyl ester. As the reaction advances, ceralure B1 acid 6 becomes visible in the reaction mixture, apparently through an $S_N2$ type epimerization at C-3 by iodide. In a separate experiment, refluxing an acetonitrile solution of NaI and ceralure B1 acid 6 partially converted the latter to the ceralure A acid 5, thus indicating the reversible nature of iodide-catalyzed epimerization. After a 2-hr reflux, an approximately 1:1 ratio of ceralure B1 acid 6 ceralure A acid 5 was reached. At 5–6 hr, an equilibrium between the two epimers appeared to occur with a ratio of about 3:2. A reaction time longer than 2 hr, however, resulted in increasing amounts of by-products and thus was not considered advantageous.

Recycling step d) reverts ceralure A acid 5 back to lactone 4 (see Example 3). A short reflux of the epimeric mixture of ceralure B1 6 and ceralure A 5 acids with potassium carbonate in tetrahydrofuran (THF) results in complete cyclization of epimer A 5 to lactone 4 whereas epimer B1 6 remains intact. Separation of remaining ceralure B1 acid 6 and lactone 4 is easily achieved by partitioning between $K_2CO_3$ (pH ~8–9) and ether-hexane (1:1). This step is carried out at 0° C. in order to avoid hydrolysis and other side-reactions of the lactone. Recycled lactone 4 may then be converted to a subsequent mixture of epimers ceralure A acid 5 and ceralure B1 acid 6. Recycled lactone 4 may also be combined with fresh lactone 4 from step b) before the conversion reaction, such as in a continuous flow process.

In step e), ceralure B1 acid 6 is esterified using a non-epimerizing procedure to yield ceralure B1 1 having about 92–94% purity. A purified ceralure B1 1 product may be obtained by flash chromatography on silica (see Example 4), or more advantageously by crystallization of the acid 5 from heptane and esterification (Example 5). The overall yield starting from trans-siglure acid 2 is approximately 58–65%.

The following examples are intended only to further illustrate the invention and are not intended to limit the scope of the invention as defined by the claims.

EXAMPLES

Melting points and boiling points were uncorrected. $^1H$ nuclear magnetic resonance (NMR) and $^{13}C\{1H\}$NMR spectra were recorded with tetramethylsilane (TMS) as an internal standard in $CDCl_3$ on a Bruker QE-300 spectrometer. $^1H$ NMR coupling constants are reported in Hz. Gas chromatography (GC) was performed on a Shimadzu 14A gas chromatograph using a 60-m SPB-608 custom made capillary column (Supelco) and $H_2$ as a carrier gas. Mass spectra were obtained with a Hewlett-Packard 5971 GC-MS equipped with 30 m DB-5 (J&W Scientific) column. Combustion analyses were conducted by Galbraith Laboratories. Unless otherwise mentioned, materials were obtained from commercial suppliers and were used without further purification.

Example 1

Formation of Iodolactone 3

Iodolactone 3 was prepared according to the procedure described by House et al. (1983, *J. Org. Chem.* vol. 48, pp. 1643–1654) from trans-siglure acid (Farma Tech International Corp., Fresno, Calif.). Crude iodolactone of 98% purity was obtained in 87% yield and was used in the following step b) without further purification. MS (EI):266 (M+), 139, 95 (100), 79, 77, 67; data corresponded with that reported in the literature. (Raw et al., supra).

Example 2

Formation of Lactone 4

The crude iodolactone from Example 1 (54.35 g, 0.204 mol) was refluxed with tributylin hydride (68 ml, 0.252 mol) in benzene solution (250 ml) in the presence of 2,2'-azobisisobutyronitrile (70 mg) for 7 hr according to procedures described by Raw et al., supra. The reaction mixture was concentrated on a rotary evaporator, diluted with ether (~200 ml) and treated with aqueous KF (40 g KF×2$H_2$O in 250 ml water) After vigorous stirring for 1 h, the mixture was filtered, the organic layer separated, and the aqueous layer extracted with ether (3×100 ml). The combined ether extract was dried ($Na_2SO_4$) and concentrated to give crude product (42.56 g)

Crude lactone (1.01 g) was purified by flash chromatography (hexane/ethyl acetate, 7:3) to give lactone (0.630 g) in 93% yield. Alternatively, >98% pure lactone could be obtained by distillation, b.p. 86–88°/0.6 mm Hg. MS(EI): 140 (M+), 112, 97, 81 (100), 55, 41; data corresponds to known values reported in the literature.

Example 3

Formation of Ceralure B1 Acid 6 with Trichloromethylsilane by Recycling Ceralure A Acid 5 to Lactone 4

To a solution of lactone 4 (3.50 g, 25 mmol) from Example 2 and sodium iodide (11.25 g, 75 mmol) in dry acetonitrile (80 ml), trichloromethylsilane (2.95 ml. 25 mmol) was added under $N_2$ atmosphere. The mixture was refluxed for 2 h, an aliquot was treated with water and extracted with ether. The ether extract was esterified with diazomethane and analyzed by GC. GC analysis showed no starting lactone present and ~51% of ceralure B1 methyl ester in the mixture. The reaction mixture was concentrated by rotary evaporation to distill most of acetonitrile; the remainder was partitioned between water (100 ml) and ether (100 ml). The water layer was extracted with ether (3×100 ml), and the combined ether extract was washed with saturated sodium thiosulfate solution and dried with $Na_2SO_4$. Evaporation of the solvent left a 6.4 g mixture of the iodoacids, which, according to GC of the corresponding methyl esters, consisted of 53% B1 and 43% A.

The mixture of the epimeric acids B1 and A was dissolved in THF (100 ml), anhydrous potassium carbonate (1.73 g, 12.5 mmol) was added, and the resultant solution was refluxed under $N_2$ atmosphere for ~1 h until the pale yellow color disappeared. GC analysis of an aliquot treated with diazomethane showed complete cyclization of epimer A to starting lactone. Tetrahydrofuran was removed under reduced pressure, water (50 ml) was added to the remainder, and the mixture was cooled to 0° C. A solution of $K_2CO_3$ (15 ml, 10%) was added under vigorous stirring, bringing the pH to 8–9. The mixture was extracted while cold with hexane:ether, 1:1 (3×30 ml), the organic extract was dried with $Na_2CO_4$ and evaporated to recover starting lactone 4 (1.40 g, 10 mmol) of 97% purity. Thus, the conversion after consecutive ring opening and lactonization steps was 60%. The aqueous layer was acidified with 10% $H_2SO_4$ to pH 2, extracted with $CH_2Cl_2$ and dried with $Na_2SO_4$. Evaporation of $CH_2Cl_2$ afforded ceralure B1 acid 6 (3.78 g, 92% purity) as a colorless solid with melting point 165° C. (heptane).

$^1H$ NMR (300 MHz, $CDCl_3$) :0.91 (d, J=6.5, $CH_3$), 1.13 (dddd, $^3J_{3a-2a} \approx {}^3J_{3a-4a} \approx {}^2J_{3a-3e} \approx 12.5$ Hz, $^3J_{3a-4a}=3.5$, H-3a), 1.64 (dm, H-3e), 1.75 (m, H-2a), 1.9–2.01 (m, 2H, H-1, H-4a), 2.16 (ddd, $^3J_{6a-1a}={}^3J_{6a-5a}={}^3J_{6a-5a}={}^2J_{6a-6e}=12.5$, H-6a), 2.42 (dm, $^2J_{4a-4e}=12.0$, H-4e), 2.61 (dm, H-6e), 4.03 (dddd, $^3J_{5a-4a}=12.5$, $^3J_{5a-6e} \approx 4.0$, H-5a).

$^{13}C$ NMR (76 MHz, $CDCl_3$): 20.1 ($CH_3$), 24.9 (C-5), 32.9 (C-2), 36.1 (C-3), 39.9 (C-4), 42.5 (C-6), 53.0 (C-1), 179.4 (COOH). Anal. Calcd. For $C_8H_{13}IO_2$:C, 35.80, H, 4.90. Found C, 36.09: H, 5.14.

Example 4

Formation of Ceralure B1 1

Ceralure B1 acid 6 from Example 3 (2.97 g, 92% purity, 11 mmol) was dissolved in $CH_2Cl_2$ (30 ml), and oxalyl chloride (1.93 ml, 22.1 mmol) was added at 0° C. followed by dimethylformamide (10 μl). The mixture was stirred at RT for 2 h and concentrated on rotary evaporator. The concentrate was taken into $CH_2Cl_2$ (18 ml), cooled to −10° C. and treated with a mixture of ethanol (734 μl, 13 mmol) and pyridine (1.06 ml, 13 mmol). After stirring for 2 h at RT, the mixture was diluted with $CH_2Cl_2$ (25 ml) and washed sequentially with water, 5% HCl, water, then dried with $Na_2SO_4$. Evaporation of the solvent left ceralure B1 1 (3.15 g) of 92% purity. A sample of crude ceralure B1 1 (105 mg) was purified by flash chromatography (hexane/ethyl acetate, 19:1) to afford 93 mg of >98% pure product. The yield of isolated ceralure B1 1 based on reacted lactone 4 (Example 3) was 80%. The overall yield based on starting material trans-siglure acid 2 was 65%. GC retention time and mass spectroscopy data of synthesized product and of an authentic sample were identical. MS(EI) m/z: 251 (2%), 169 (15), 123 (10), 95 (100), 81 (12), 67 (22) 55 (25).

Example 5

Formation of Ceralure B1 1

Ceralure B1 acid 6 from Example 3 (5.04 g, 92% purity) was purified by crystallization from heptane (180 ml) to afford 98% ceralure B1 acid 6 (4.18 9, 15.60 mmol). The product was dissolved in $CH_2Cl_2$ (50 ml), sequentially treated with oxalyl chloride (2.74 ml, 31.32 mmol), and DMF (14 μl) and esterified as described in Example 4. Evaporation of the solvent left 98% ceralure B1 1 (4.25 g, 14.36 mmol). The yield based on reacted lactone 4 (from Example 3) was 72%. Th e overall yield starting from trans-siglure acid 2 was 58%.

Example 6

Formation of Mixture of Ceralure A Acid 5 and Ceralure B1 Acid 6 From Lactone 4 with Trimethylchlorosilane To a solution of lactone 4 from Example 2 (1.0 g, 7.1 mmol) and NaI (3.15 b, 21 mmol) in acetonitrile (20 ml) was added under $N_2$ trimethylchlorosilane (2.7 ml, 21 mmol). The mixture was refluxed for 30 min, then quenched with ice-water. The reaction products were extracted with ether (3×20 ml), and the combined ether extract was washed with sodium thiosulfate and dried. Evaporation of the solvent provided a mixture of 32% starting lactone 4 5% epimer B1 6 and 60% epimer A 5. The mixture was suspended in water and treated with 10% $K_2CO_3$ at 0° C. to pH ~9 and extracted with 1:1 mixture of hexane and ether (4×20 ml) to separate unreacted lactone from acids. The aqueous layer was acidified to pH ~2 with 10% $H_2SO_4$ to liberate the acids which were extracted with $CH_2Cl_2$ (4×20 ml). After drying the extract with $Na_2SO_4$, the residue was purified by flash chromatography (hexane/ethyl acetate, 4:1, 0.01% trifluoroacetic acid) to afford 430 mg of the 97% pure ceralure A acid 5, mp 86° C.

$^1H$ NMR (300 MHz, $CDCl_3$) : 1.01 (d, J=6.5, $CH_3$), 1.47–1.85 (m, 5H, H-2a, 3a, 3e, 4a, 6a), 2.06 (m, 1H, H-4e), 2.25 (dm, $^2J_{6e-6a}=14.5$, H-6e), 2.55 (ddd, $^3J_{1a-6e}=3.0$ Hz, $^3J_{1a-2} \approx {}^3J_{1a-6a} \approx 11.0$, H-1a), 4.84 (m, 1H, H-5e), 11.15 (1H, OH).

$^{13}C$ NMR (76 MHz, $CDCl_3$): 20.1 ($CH_3$), 30.2, 32.0, 33.7 (C-5), 35.6 (C-4), 38.8 (C-6), 47.4 (C-1), 181.5 (COOH). Anal. Calcd. for $C_8H_{13}IO_2$: C, 35.80; H, 4.90. Found: C, 35.26; H, 4.99.

Running the same reaction for 7–8 h resulted in complete conversion of the starting lactone to the 42:53 mixture of epimers B1 and A. This could be used to make ceralure B1 acid 6 as described in Example 3 by cyclizing epimer A to lactone 4 for recycling.

All references cited hereinabove are hereby incorporated by reference in their entirety.

I claim:

1. A method for the preparation of ceralure B1

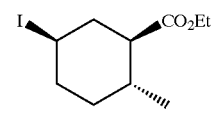

said method comprising (a) converting trans-siglure acid

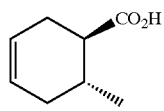

to iodolactone

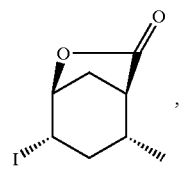

(b) reducing iodolactone

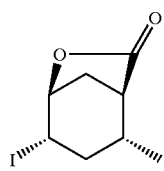

to lactone

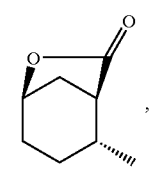

(c) converting lactone

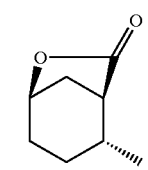

to a mixture of epimers ceralure A acid

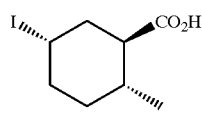

and ceralure B1 acid

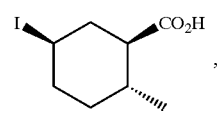

(d) recycling ceralure A acid

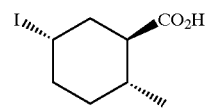

to lactone

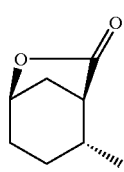

and separating remaining ceralure B1 acid

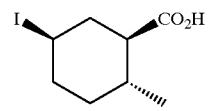

from lactone

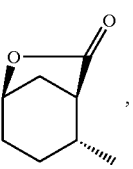

and (e) esterifying ceralure B1 acid

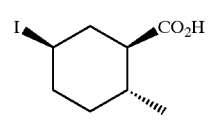

to produce ceralure B1

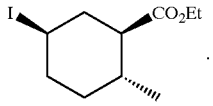

2. The method of claim 1, wherein step (c) is repeated to produce a mixture of epimers ceralure A acid

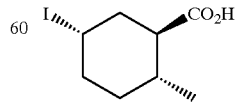 and ceralure B1 acid 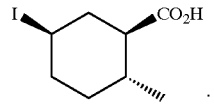.

3. The method of claim 1, wherein (−)-trans-siglure acid is used as starting material to produce (−)ceralure B1.

4. The method of claim 1, wherein ceralure B1
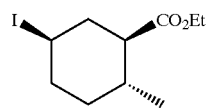
is purified by chromatography, or ceralure B1 acid
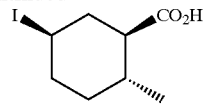
is purified by crystallization prior to esterification.
* * * * *